United States Patent [19]
Wingert et al.

[11] Patent Number: 5,118,710
[45] Date of Patent: Jun. 2, 1992

[54] SULFUR-CONTAINING ACRYLIC ESTERS AND FUNGICIDES CONTAINING THEM

[75] Inventors: Horst Wingert; Hubert Sauter, both of Mannheim; Franz Schuetz, Ludwigshafen; Bernd Wenderoth, Lampertheim; Siegbert Brand, Weinheim; Bernd Mueller, Frankenthal; Franz Roehl, Ludwigshafen; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 634,811

[22] Filed: Dec. 31, 1990

Related U.S. Application Data

[63] Continuation of Ser. No. 451,239, Dec. 15, 1989, abandoned.

[30] Foreign Application Priority Data

Jan. 20, 1989 [DE] Fed. Rep. of Germany ....... 3901607

[51] Int. Cl.$^5$ .............. A61K 31/275; A61K 31/235; A61K 31/10; C07C 323/07
[52] U.S. Cl. .................... 514/522; 514/539; 514/544; 514/568; 514/569; 558/416; 560/10; 560/17; 562/426; 562/427; 562/431
[58] Field of Search .............. 560/10, 17; 562/426, 562/427, 431; 558/416; 514/522, 568, 569, 539, 544

[56] References Cited

FOREIGN PATENT DOCUMENTS 226917 7/1987 European Pat. Off. .
278595 8/1988 European Pat. Off. .
299694 1/1989 European Pat. Off. .

Primary Examiner—Arthur C. Prescott
Assistant Examiner—Vera C. Clarke
Attorney, Agent, or Firm—Oblon, Spivak, McClelland, Maier & Neustadt

[57] ABSTRACT

Acrylic esters of the formula

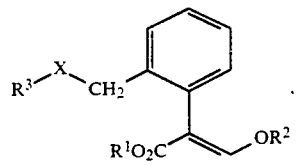

where $R^1$ and $R^2$ are hydrogen or alkyl, X is S, SO or $SO_2$, $R^3$ is phenyl, naphthyl or phenanthrenyl, these radicals being unsubstituted or substituted, with the exception of compounds in which $R^3$ is phenyl, 3-chlorophenyl, 4-chlorophenyl, 2,4-dichlorophenyl or methylphenyl, and fungicides containing these compounds.

8 Claims, No Drawings

SULFUR-CONTAINING ACRYLIC ESTERS AND FUNGICIDES CONTAINING THEM

The present invention relates to novel acrylic ester derivatives, methods of preparing them, fungicides containing them, and their use as fungicides.

The use of acrylic esters, for example methyl α-(2-[4-chlorophenylthiomethyl]phenyl)-β-methoxyacrylate (EP 226 917) and methyl α-(2-[3-chlorophenylthiomethyl]phenyl)-β-methoxyacrylate (EP 278 595), as fungicides has been disclosed.

We have now found that substituted acrylic ester derivatives of the general formula

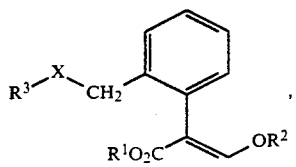

I where $R^1$ and $R^2$ are hydrogen or $C_1$-$C_5$-alkyl, X is S, SO or $SO_2$, $R^3$ is phenyl, naphthyl or phenanthrenyl, these radicals being unsubstituted or substituted by halogen, cyano, nitro, formyl, $C_1$-$C_{10}$-alkyl, $C_1$-$C_4$-alkoxy, $C_1$-$C_2$-haloalkyl, aryl or $C_1$-$C_4$-alkoxycarbonyl, with the exception of compounds in which $R^3$ is phenyl, 3-chlorophenyl, 4-chlorophenyl, 2,4-dichlorophenyl or methylphenyl, have a fungicidal action superior to that of the abovementioned prior art compounds.

The radicals listed in formula I may for example have the following meanings:

$R^1$ and $R^2$ are identical or different and denote for instance hydrogen, $C_1$-$C_5$-alkyl, methyl, ethyl, propyl, isopropyl, butyl and pentyl; methyl is preferred.

X may be S, SO or $SO_2$; S is preferred.

$R^3$ may for example be phenyl, naphthyl and phenanthrenyl, the rings being unsubstituted or substituted by from one to five of the following radicals:

halogen (e.g., fluorine, chlorine, bromine), cyano, nitro, formyl, $C_1$-$C_{10}$-alkyl (e.g., methyl, ethyl, n- or isopropyl; n-, iso-, sec.- or tert.-butyl; n-, iso-, sec.-, tert.- or neopentyl; hexyl, heptyl, octyl, nonyl, decyl), $C_1$-$C_2$-haloalkyl (e.g., difluoromethyl, trifluoromethyl, chloromethyl, dichloromethyl, trichloromethyl, pentafluoroethyl), $C_1$-$C_4$-alkoxy (e.g., methoxy, ethoxy, n- or isopropoxy; n-, iso-, sec.- or tert.-butoxy), aryl (e.g., phenyl, naphthyl) and $C_1$-$C_4$-alkoxycarbonyl (e.g., methoxycarbonyl, ethoxycarbonyl, propoxycarbonyl, butoxycarbonyl).

The novel compounds of the formula I may, because of the C=C double bond, be present both as E and Z isomers. Both the individual isomeric compounds and mixtures thereof are encompassed by the invention and may be used as fungicides.

The novel compounds of the general formula I (X=S) may for example be prepared by reacting a thiol of the formula II with a benzyl bromide of the general formula III.

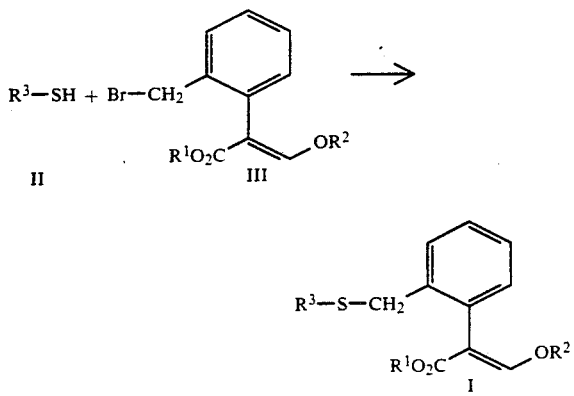

$R^1$, $R^2$ and $R^3$ have the meanings given in claim 1.

The reactions to give compounds of the formula I may be carried out for instance in inert solvents or diluents (e.g., acetone, acetonitrile, dimethyl sulfoxide, dioxane, dimethylformamide, N-methylpyrrolidone, N,N'-dimethylpropyleneurea and pyridine) using a base (e.g., sodium carbonate, potassium carbonate). It may also be advantageous to add a catalyst, e.g., tris-(3,6-dioxoheptyl)-amine (J. Org. Chem. 50 (1985) 3717), to the reaction mixture.

Alternatively, the compounds of the general formula II may also be converted first with a base (e.g., sodium hydroxide or potassium hydroxide) into the corresponding sodium or potassium salts, which are then reacted in an inert solvent or diluent (e.g., dimethylformamide) with the benzyl bromide of the formula III to give the corresponding compounds of the general formula I.

The thiols of the general formula $R^3$—SH ($R^3$ having the above meanings) are either known or may be prepared by methods analogous to known methods. Such manufacturing methods are disclosed for instance in Houben-Weyl, Methoden der organischen Chemie VI/3, p. 54 et seq. (1955). α-Bromomethylphenylacrylic esters of the general formula III are known from DE-35 19 280, DE-35 45 318 and DE-35 45 319.

The novel compounds of the general formula I (where X=SO or $SO_2$) are obtained by oxidation of the corresponding thiethers of the general formula I (wherein X=S). Oxidation may be carried out for instance with peroxo compounds such as meta-chloroperbenzoic acid in an inert solvent such as toluene.

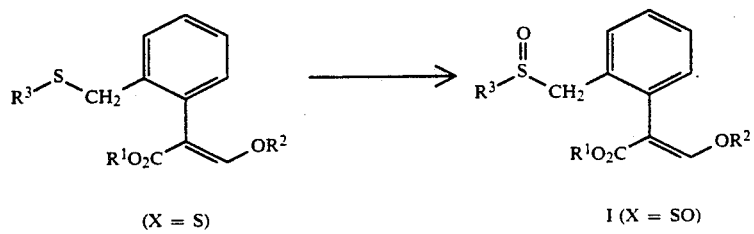

(X = S)     I (X = SO)

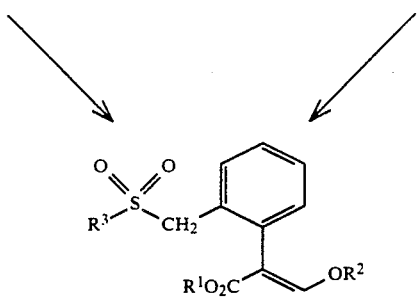

I (X = SO₂)

(see e.g. Houben-Weyl, Methoden der Org. Chemie IX, 213, 228 (1955)).

EXAMPLES

The following directions illustrate the manufacture of the novel active ingredients.

EXAMPLE 1

Methyl α-(2-naphthylthiomethylphenyl)-β-methoxyacrylate (compound 2, Table 1)

8 g of methyl α-(2-bromomethylphenyl)-β-methoxyacrylate, 4.5 g of 2-thionaphthol, 4.4 g of potassium carbonate and 100 mg of potassium iodide are refluxed for 20 hours in 200 ml of acetone. 200 ml of water is then added and extraction is carried out three times with methylene chloride. The organic phases are dried over $Na_2SO_4$ and evaporated down. The oil which remains is chromatographed on silica gel using a mixture of n-hexane and ethyl acetate. There is obtained 8.19 g of slightly yellow crystals of melting point 52°–58° C.

EXAMPLE 2

Methyl α-(2-naphthylsulfoxymethylphenyl)-β-methoxyacrylate (compound 2, Table 2) and methyl α-(2-naphthylsulfonemethylphenyl)-β-methoxyacrylate (compound 2, Table 3)

5.91 g of the methyl α-(2-naphthylthiomethylphenyl)-β-methoxyacrylate obtained according to Example 1 are stirred for 18 hours at room temperature with 5.0 g of 3-chlorperobenzoic acid in 100 ml of toluene. 50 ml of ethyl acetate is added, and the mixture is extracted by shaking twice with sodium bicarbonate solution, dried and evaporated down. The oil which remains is chromatographed on silica gel using a mixture of n-hexane and ethyl acetate. There is obtained 660 mg of compound 2 (Table 3) as a colorless solid (m.p. 130°–134° C.) and 3.72 g of compound 2 (Table 2) as an oil.

The following compounds may be obtained in a similar manner:

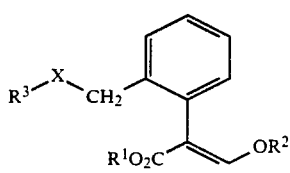

I

TABLE 1

| No. | R³ | R¹ | R² | IR (cm⁻¹) (mp.) |
|---|---|---|---|---|
| 1 | 1-naphthyl | CH₃ | CH₃ | |
| 2 | 2-naphthyl | CH₃ | CH₃ | 52–58° C. |
| 3 | 3-phenanthrenyl | CH₃ | CH₃ | |
| 4 | 2-chlorophenyl | CH₃ | CH₃ | 97–99° C. |
| 5 | 2-bromophenyl | CH₃ | CH₃ | 121–127° C. |
| 6 | 3-bromophenyl | CH₃ | CH₃ | 84–86° C. |
| 7 | 4-bromophenyl | CH₃ | CH₃ | 84–91° C. |
| 8 | 2-fluorophenyl | CH₃ | CH₃ | 84–88° C. |
| 9 | 3-fluorophenyl | CH₃ | CH₃ | 77–82° C. |
| 10 | 4-fluorophenyl | CH₃ | CH₃ | 50–54° C. |
| 11 | 2-ethylphenyl | CH₃ | CH₃ | |
| 12 | 3-ethylphenyl | CH₃ | CH₃ | |
| 13 | 4-ethylphenyl | CH₃ | CH₃ | |
| 14 | 2-isopropylphenyl | CH₃ | CH₃ | |
| 15 | 3-isopropylphenyl | CH₃ | CH₃ | |
| 16 | 4-isopropylphenyl | CH₃ | CH₃ | |
| 17 | 2-tert-butylphenyl | CH₃ | CH₃ | |
| 18 | 3-tert-butylphenyl | CH₃ | CH₃ | |
| 19 | 4-tert-butylphenyl | CH₃ | CH₃ | |
| 20 | 4-butylphenyl | CH₃ | CH₃ | |
| 21 | 4-hexylphenyl | CH₃ | CH₃ | |
| 22 | 4-nonylphenyl | CH₃ | CH₃ | |
| 23 | 4-decylphenyl | CH₃ | CH₃ | |
| 24 | 2-methoxyphenyl | CH₃ | CH₃ | 77–85° C. |
| 25 | 3-methoxyphenyl | CH₃ | CH₃ | 52–58° C. |
| 26 | 4-methoxyphenyl | CH₃ | CH₃ | 70–72° C. |
| 27 | 2-trifluoromethylphenyl | CH₃ | CH₃ | |
| 28 | 3-trifluoromethylphenyl | CH₃ | CH₃ | |
| 29 | 4-trifluoromethylphenyl | CH₃ | CH₃ | |
| 30 | 4-formylphenyl | CH₃ | CH₃ | |
| 31 | 2-nitrophenyl | CH₃ | CH₃ | |
| 32 | 3-nitrophenyl | CH₃ | CH₃ | |
| 33 | 4-nitrophenyl | CH₃ | CH₃ | |
| 34 | 2,5-dichlorophenyl | CH₃ | CH₃ | 69–73° C. |
| 35 | 2,6-dichlorophenyl | CH₃ | CH₃ | 113–116° C. |
| 36 | 3,4-dichlorophenyl | CH₃ | CH₃ | 99–104° C. |
| 37 | 2,3-dichlorophenyl | CH₃ | CH₃ | |
| 38 | 3,5-dichlorophenyl | CH₃ | CH₃ | |
| 39 | 2,3,4-trichlorophenyl | CH₃ | CH₃ | |
| 40 | 2,4,5-trichlorophenyl | CH₃ | CH₃ | |
| 41 | 2,4,6-trichlorophenyl | CH₃ | CH₃ | |
| 42 | 2,3,4,6-tetrachlorophenyl | CH₃ | CH₃ | |
| 43 | 2,3,4,5,6-pentachlorophenyl | CH₃ | CH₃ | 145–150° C. |
| 44 | 2,3,4,5-tetrafluorophenyl | CH₃ | CH₃ | |
| 45 | 2,3,5,6-tetrafluorophenyl | CH₃ | CH₃ | |
| 46 | 2,3,4,5,6-pentafluorophenyl | CH₃ | CH₃ | 80–83° C. |
| 47 | 2-chloro, 4-fluorophenyl | CH₃ | CH₃ | |
| 48 | 3-chloro, 4-fluorophenyl | CH₃ | CH₃ | |
| 49 | 2-chloro, 6-methylphenyl | CH₃ | CH₃ | |
| 50 | 4-chloro, 2-methylphenyl | CH₃ | CH₃ | |
| 51 | 2,4-dichloro, 5-methylphenyl | CH₃ | CH₃ | |
| 52 | 4-chloro, 2,5-dimethylphenyl | CH₃ | CH₃ | |
| 53 | 4-bromo, 3-methylphenyl | CH₃ | CH₃ | |
| 54 | 3,5-bistrifluoromethylphenyl | CH₃ | CH₃ | |
| 56 | 2,5-dimethylphenyl | CH₃ | CH₃ | 1708,1634,1486, 1435,1283,1256, 1197,1126,1093, 768 |

TABLE 1-continued

X = S

| No. | R³ | R¹ | R² | IR (cm⁻¹) (mp.) |
|---|---|---|---|---|
| 57 | 2,4-dimethylphenyl | CH₃ | CH₃ | 57-62° C. |
| 58 | 2,5-dimethylphenyl | CH₃ | CH₃ | |
| 59 | 2,6-dimethylphenyl | CH₃ | CH₃ | |
| 60 | 3,4-dimethylphenyl | CH₃ | CH₃ | 1708,1633,1487, 1434,1283,1256, 1192,1126,1095, 768 |
| 61 | 3,5-dimethylphenyl | CH₃ | CH₃ | |
| 62 | 2,4,5-trimethylphenyl | CH₃ | CH₃ | |
| 63 | 2,6-diethylphenyl | CH₃ | CH₃ | |
| 64 | 2,4-di-tert.-butylphenyl | CH₃ | CH₃ | |
| 65 | 2,5-dimethoxyphenyl | CH₃ | CH₃ | |
| 66 | 3,4-dimethoxyphenyl | CH₃ | CH₃ | |
| 67 | 2-methyl, 4-tert.-butylphenyl | CH₃ | CH₃ | |
| 68 | 2-methoxycarbonylphenyl | CH₃ | CH₃ | |
| 69 | 2-ethoxycarbonylphenyl | CH₃ | CH₃ | |
| 70 | 2-propoxycarbonylphenyl | CH₃ | CH₃ | |
| 71 | 2-butoxycarbonylphenyl | CH₃ | CH₃ | |
| 72 | 2-cyanophenyl | CH₃ | CH₃ | |
| 73 | 3-cyanophenyl | CH₃ | CH₃ | |
| 74 | 4-cyanophenyl | CH₃ | CH₃ | |
| 75 | phenyl | CH₃ | Et | |
| 76 | phenyl | Et | CH₃ | |
| 77 | phenyl | CH₃ | n-Bu | |
| 78 | phenyl | n-Bu | n-Bu | |

TABLE 2

(X = SO)

| No. | R³ | R¹ | R² | IR (cm⁻¹) (mp.) |
|---|---|---|---|---|
| 1 | 1-naphthyl | CH₃ | CH₃ | |
| 2 | 2-naphthyl | CH₃ | CH₃ | 1705,1632,1285, 1258,1197,1126, 1091,1067,1044, 771 |
| 3 | 3-phenanthrenyl | CH₃ | CH₃ | |
| 4 | 2-chlorophenyl | CH₃ | CH₃ | |
| 5 | 2-bromophenyl | CH₃ | CH₃ | |
| 6 | 3-bromophenyl | CH₃ | CH₃ | |
| 7 | 4-bromophenyl | CH₃ | CH₃ | 112-117° C. |
| 8 | 2-fluorophenyl | CH₃ | CH₃ | |
| 9 | 3-fluorophenyl | CH₃ | CH₃ | |
| 10 | 4-fluorophenyl | CH₃ | CH₃ | 75-80° C. |
| 11 | 2-ethylphenyl | CH₃ | CH₃ | |
| 12 | 3-ethylphenyl | CH₃ | CH₃ | |
| 13 | 4-ethylphenyl | CH₃ | CH₃ | |
| 14 | 2-isopropylphenyl | CH₃ | CH₃ | |
| 15 | 3-isopropylphenyl | CH₃ | CH₃ | |
| 16 | 4-isopropylphenyl | CH₃ | CH₃ | |
| 17 | 2-tert-butylphenyl | CH₃ | CH₃ | |
| 18 | 3-tert-butylphenyl | CH₃ | CH₃ | |
| 19 | 4-tert-butylphenyl | CH₃ | CH₃ | |
| 20 | 4-butylphenyl | CH₃ | CH₃ | |
| 21 | 4-hexylphenyl | CH₃ | CH₃ | |
| 22 | 4-nonylphenyl | CH₃ | CH₃ | |
| 23 | 4-decylphenyl | CH₃ | CH₃ | |
| 24 | 2-methoxyphenyl | CH₃ | CH₃ | |
| 25 | 3-methoxyphenyl | CH₃ | CH₃ | 1706,1633,1594, 1481,1285,1252, 1198,1126,1092, 1042,772 |
| 26 | 4-methoxyphenyl | CH₃ | CH₃ | |
| 27 | 2-trifluoromethylphenyl | CH₃ | CH₃ | |
| 28 | 3-trifluoromethylphenyl | CH₃ | CH₃ | |
| 29 | 4-trifluoromethylphenyl | CH₃ | CH₃ | |
| 30 | 4-formylphenyl | CH₃ | CH₃ | |
| 31 | 2-nitrophenyl | CH₃ | CH₃ | |
| 32 | 3-nitrophenyl | CH₃ | CH₃ | |
| 33 | 4-nitrophenyl | CH₃ | CH₃ | |
| 34 | 2,5-dichlorophenyl | CH₃ | CH₃ | |
| 35 | 2,6-dichlorophenyl | CH₃ | CH₃ | |
| 36 | 3,4-dichlorophenyl | CH₃ | CH₃ | 97-102° C. |
| 37 | 2,3-dichlorophenyl | CH₃ | CH₃ | |
| 38 | 3,5-dichlorophenyl | CH₃ | CH₃ | |
| 39 | 2,3,4-trichlorophenyl | CH₃ | CH₃ | |
| 40 | 2,4,5-trichlorophenyl | CH₃ | CH₃ | |

TABLE 2-continued (X = SO)

| No. | R³ | R¹ | R² | IR (cm⁻¹) (mp.) |
|---|---|---|---|---|
| 41 | 2,4,6-trichlorophenyl | CH₃ | CH₃ | |
| 42 | 2,3,4,6-tetrachlorophenyl | CH₃ | CH₃ | |
| 43 | 2,3,4,5,6-pentachlorophenyl | CH₃ | CH₃ | |
| 44 | 2,3,4,5-tetrafluorophenyl | CH₃ | CH₃ | |
| 45 | 2,3,5,6-tetrafluorophenyl | CH₃ | CH₃ | |
| 46 | 2,3,4,5,6-pentafluorophenyl | CH₃ | CH₃ | |
| 47 | 2-chloro, 4-fluorophenyl | CH₃ | CH₃ | |
| 48 | 3-chloro, 4-fluorophenyl | CH₃ | CH₃ | |
| 49 | 2-chloro, 6-methylphenyl | CH₃ | CH₃ | |
| 50 | 4-chloro, 2-methylphenyl | CH₃ | CH₃ | |
| 51 | 2,4-dichloro, 5-methylphenyl | CH₃ | CH₃ | |
| 52 | 4-chloro, 2,5-dimethylphenyl | CH₃ | CH₃ | |
| 53 | 4-bromo, 3-methylphenyl | CH₃ | CH₃ | |
| 54 | 3,5-bistrifluoromethylphenyl | CH₃ | CH₃ | |
| 56 | 2,5-dimethylphenyl | CH₃ | CH₃ | |
| 57 | 2,4-dimethylphenyl | CH₃ | CH₃ | |
| 58 | 2,5-dimethylphenyl | CH₃ | CH₃ | |
| 59 | 2,6-dimethylphenyl | CH₃ | CH₃ | |
| 60 | 3,4-dimethylphenyl | CH₃ | CH₃ | |
| 61 | 3,5-dimethylphenyl | CH₃ | CH₃ | |
| 62 | 2,4,5-trimethylphenyl | CH₃ | CH₃ | |
| 63 | 2,6-diethylphenyl | CH₃ | CH₃ | |
| 64 | 2,4-di-tert.-butylphenyl | CH₃ | CH₃ | |
| 65 | 2,5-dimethoxyphenyl | CH₃ | CH₃ | |
| 66 | 3,4-dimethoxyphenyl | CH₃ | CH₃ | |
| 67 | 2-methyl, 4-tert.-butylphenyl | CH₃ | CH₃ | |
| 68 | 2-methoxycarbonylphenyl | CH₃ | CH₃ | |
| 69 | 2-ethoxycarbonylphenyl | CH₃ | CH₃ | |
| 70 | 2-propoxycarbonylphenyl | CH₃ | CH₃ | |
| 71 | 2-butoxycarbonylphenyl | CH₃ | CH₃ | |
| 72 | 2-cyanophenyl | CH₃ | CH₃ | |
| 73 | 3-cyanophenyl | CH₃ | CH₃ | |
| 74 | 4-cyanophenyl | CH₃ | CH₃ | |
| 75 | phenyl | CH₃ | Et | |
| 76 | phenyl | Et | CH₃ | |
| 77 | phenyl | CH₃ | n-Bu | |
| 78 | phenyl | n-Bu | n-Bu | |

TABLE 3

(X = SO₂)

| No. | R³ | R¹ | R² | IR (cm⁻¹) (mp.) |
|---|---|---|---|---|
| 1 | 1-naphthyl | CH₃ | CH₃ | |
| 2 | 2-naphthyl | CH₃ | CH₃ | 130-134° C. |
| 3 | 3-phenanthrenyl | CH₃ | CH₃ | |
| 4 | 2-chlorophenyl | CH₃ | CH₃ | |
| 5 | 2-bromophenyl | CH₃ | CH₃ | |
| 6 | 3-bromophenyl | CH₃ | CH₃ | |
| 7 | 4-bromophenyl | CH₃ | CH₃ | 168-173° C. |
| 8 | 2-fluorophenyl | CH₃ | CH₃ | |
| 9 | 3-fluorophenyl | CH₃ | CH₃ | |
| 10 | 4-fluorophenyl | CH₃ | CH₃ | 140-145° C. |
| 11 | 2-ethylphenyl | CH₃ | CH₃ | |
| 12 | 3-ethylphenyl | CH₃ | CH₃ | |
| 13 | 4-ethylphenyl | CH₃ | CH₃ | |
| 14 | 2-isopropylphenyl | CH₃ | CH₃ | |
| 15 | 3-isopropylphenyl | CH₃ | CH₃ | |
| 16 | 4-isopropylphenyl | CH₃ | CH₃ | |
| 17 | 2-tert-butylphenyl | CH₃ | CH₃ | |
| 18 | 3-tert-butylphenyl | CH₃ | CH₃ | |
| 19 | 4-tert-butylphenyl | CH₃ | CH₃ | |
| 20 | 4-butylphenyl | CH₃ | CH₃ | |
| 21 | 4-hexylphenyl | CH₃ | CH₃ | |
| 22 | 4-nonylphenyl | CH₃ | CH₃ | |
| 23 | 4-decylphenyl | CH₃ | CH₃ | |
| 24 | 2-methoxyphenyl | CH₃ | CH₃ | |
| 25 | 3-methoxyphenyl | CH₃ | CH₃ | 1698,1627,1296, 1255,1142,1126, 1096 |
| 26 | 4-methoxyphenyl | CH₃ | CH₃ | |
| 27 | 2-trifluoromethylphenyl | CH₃ | CH₃ | |
| 28 | 3-trifluoromethylphenyl | CH₃ | CH₃ | |
| 29 | 4-trifluoromethylphenyl | CH₃ | CH₃ | |
| 30 | 4-formylphenyl | CH₃ | CH₃ | |
| 31 | 2-nitrophenyl | CH₃ | CH₃ | |
| 32 | 3-nitrophenyl | CH₃ | CH₃ | |

TABLE 3-continued (X = SO$_2$)

| No. | R$^3$ | R$^1$ | R$^2$ | IR (cm$^{-1}$) (mp.) |
|---|---|---|---|---|
| 33 | 4-nitrophenyl | CH$_3$ | CH$_3$ | |
| 34 | 2,5-dichlorophenyl | CH$_3$ | CH$_3$ | |
| 35 | 2,6-dichlorophenyl | CH$_3$ | CH$_3$ | |
| 36 | 3,4-dichlorophenyl | CH$_3$ | CH$_3$ | 163-167° C. |
| 37 | 2,3-dichlorophenyl | CH$_3$ | CH$_3$ | |
| 38 | 3,5-dichlorophenyl | CH$_3$ | CH$_3$ | |
| 39 | 2,3,4-trichlorophenyl | CH$_3$ | CH$_3$ | |
| 40 | 2,4,5-trichlorophenyl | CH$_3$ | CH$_3$ | |
| 41 | 2,4,6-trichlorophenyl | CH$_3$ | CH$_3$ | |
| 42 | 2,3,4,6-tetrachlorophenyl | CH$_3$ | CH$_3$ | |
| 43 | 2,3,4,5,6-pentachlorophenyl | CH$_3$ | CH$_3$ | |
| 44 | 2,3,4,5-tetrafluorophenyl | CH$_3$ | CH$_3$ | |
| 45 | 2,3,5,6-tetrafluorophenyl | CH$_3$ | CH$_3$ | |
| 46 | 2,3,4,5,6-pentafluorophenyl | CH$_3$ | CH$_3$ | |
| 47 | 2-chloro, 4-fluorophenyl | CH$_3$ | CH$_3$ | |
| 48 | 3-chloro, 4-fluorophenyl | CH$_3$ | CH$_3$ | |
| 49 | 2-chloro, 6-methylphenyl | CH$_3$ | CH$_3$ | |
| 50 | 4-chloro, 2-methylphenyl | CH$_3$ | CH$_3$ | |
| 51 | 2,4-dichloro, 5-methylphenyl | CH$_3$ | CH$_3$ | |
| 52 | 4-chloro, 2,5-dimethylphenyl | CH$_3$ | CH$_3$ | |
| 53 | 4-bromo, 3-methylphenyl | CH$_3$ | CH$_3$ | |
| 54 | 3,5-bistrifluoromethylphenyl | CH$_3$ | CH$_3$ | |
| 56 | 2,5-dimethylphenyl | CH$_3$ | CH$_3$ | |
| 57 | 2,4-dimethylphenyl | CH$_3$ | CH$_3$ | |
| 58 | 2,5-dimethylphenyl | CH$_3$ | CH$_3$ | |
| 59 | 2,6-dimethylphenyl | CH$_3$ | CH$_3$ | |
| 60 | 3,4-dimethylphenyl | CH$_3$ | CH$_3$ | |
| 61 | 3,5-dimethylphenyl | CH$_3$ | CH$_3$ | |
| 62 | 2,4,5-trimethylphenyl | CH$_3$ | CH$_3$ | |
| 63 | 2,6-diethylphenyl | CH$_3$ | CH$_3$ | |
| 64 | 2,4-di-tert.-butylphenyl | CH$_3$ | CH$_3$ | |
| 65 | 2,5-dimethoxyphenyl | CH$_3$ | CH$_3$ | |
| 66 | 3,4-dimethoxyphenyl | CH$_3$ | CH$_3$ | |
| 67 | 2-methyl, 4-tert.-butylphenyl | CH$_3$ | CH$_3$ | |
| 68 | 2-methoxycarbonylphenyl | CH$_3$ | CH$_3$ | |
| 69 | 2-ethoxycarbonylphenyl | CH$_3$ | CH$_3$ | |
| 70 | 2-propoxycarbonylphenyl | CH$_3$ | CH$_3$ | |
| 71 | 2-butoxycarbonylphenyl | CH$_3$ | CH$_3$ | |
| 72 | 2-cyanophenyl | CH$_3$ | CH$_3$ | |
| 73 | 3-cyanophenyl | CH$_3$ | CH$_3$ | |
| 74 | 4-cyanophenyl | CH$_3$ | CH$_3$ | |
| 75 | phenyl | CH$_3$ | Et | |
| 76 | phenyl | Et | CH$_3$ | |
| 77 | phenyl | CH$_3$ | n-Bu | |
| 78 | phenyl | n-Bu | n-Bu | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia* species in cotton and lawns,
*Ustilago* species in cereals and sugar cane,
*Venturia inaequalis* (scab) in apples,
*Helminthosporium* species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Fusarium* and *Verticillium* species in various plants,
*Plasmorpara viticola* in grapes,
*Alternaria* species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt. % of active ingredient. The application rates are from 0.02 to 3 kg or more of active ingredient per hectare, depending on the type of effect desired. The novel compounds may also be used for protecting materials, for example against *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Example of formulations are given below.

I. 90 parts by weight of compound no. 2 (Table 1) is mixed with 10 parts by weight of N-methyl-α-pyrrolidone. A mixture is obtained which is suitable for application in the form of very fine drops.

II. 20 parts by weight of compound no. 4 (Table 1) is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of adduct of 40 moles of ethylene oxide and 1 mole of castor oil. By pouring the solution into water and uniformly distributing it therein, an aqueous dispersion is obtained.

III. 20 parts by weight of compound no. 25 (Table 1) is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 34 (Table 1) is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 2 (Table 1) is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 4 (Table 1) is intimately mixed with 97 parts by weight of particulate kaolin. A dust is obtained containing 3% by weight of the active ingredient.

VII. 30 parts by weight of compound no. 25 (Table 1) is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 34 (Table 1) is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 2 (Table 1) is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizer. Admixture with other fungicides frequently results in an increase in the fungicidal spectrum.

The following list of fungicides with which the novel compounds may be combined is intended to illustrate possible combinations but not to impose any restrictions.

Example of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc, N,N'-propylenebisdithiocarbamate and
N,N'-polypropylenebis(thiocarbamyl) dissulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate
2,4-dichloro-6-(o-chloroanilino)-s-triazine,
0,0-diethyl phthalimidophosphonothioate,
5-amino-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5carboxanilido-6-methyl-1,4-oxathiyne,
2,3-dihydro-5carboxanilido-6-methyl-1,4-oxathiyne 4,4-dioxide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-01,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1yl)-butan-2-one,
1-(4-chlorophenoxy)-3,3-dimethyl-1-(1H-1,2,4-triazol-1yl)-butan-2-ol,
1-(4-phenylphenoxy)-3,3-dimethyl-1(1H-1,2,4-triazol-1-yl)-2butanol,
α-(2-chlorophenyl)-α-(4-chlorophenyl)-5-pyrimidinemethanol,
5-butyl-(2-dimethylamino-4-hydroxy-6-methylpyrimidine, bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4dione,
3(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H, 1,2,4-triazole.

USE EXAMPLES

The compounds methyl α-(2-[3-chlorophenylthiomethyl]-phenyl)-β-methoxyacrylate (A) disclosed in EP 278,595 and methylα-(2-[4-chlorophenylthiomethyl]-phenyl)-β-methoxyacrylate (B) disclosed in EP 226,917 were used as comparative active ingredients.

USE EXAMPLE 1

Action on wheat brown rust

Leaves of pot-grown wheat seedlings of the "Kanzler" variety were dusted with spores of brown rust (*Puccinia recondita*). The pots were then placed for 24 hours at 20° to 22° C. in a high-humidity (90-95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 4 and 34 (Table 1), applied as 0.025 wt. % spray liquors, have a better fungicidal action (94%) than prior art active ingredients A (65%) and B (80%).

USE EXAMPLE 2

Leaves of pot-grown rice seedlings of the "Bahia" variety were sprayed to runoff with aqueous emulsions containing (dry basis) 80% of active ingredient and 20% of emulsifier, and inoculated 24 hours later with an aqueous spore suspension of *Pyricularia oryzae*. The plants were then set up in a climatic cabinet at 22°-24° C. and a relative humidity of 95-99%. The extent of fungus spread was determined after 6 days.

The results show that active ingredients 2, 4, 25 and 34 (Table 1), applied as 0.05% spray liquors, have a better fungicidal action (94%) than prior art comparative active ingredients A (65%) and B (55%).

We claim:

1. An acrylic ester of the formula:

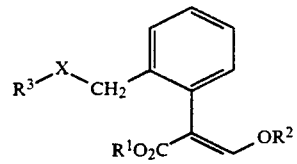

where $R^1$ and $R^2$ are hydrogen or $C_1$-$C_5$-alkyl, X is S, $R^3$ is unsubstituted naphthyl, unsubstituted phenanthrenyl, substituted phenyl, substituted naphthyl or substituted phenanthrenyl, wherein the substituents are halogen, cyano, nitro, formyl, $C_1$-$C_{10}$-alkyl, $C_1$-$C_4$-alkoxy, $C_1$-$C_2$-haloalkyl, aryl or $C_1$-$C_4$-alkoxycarbonyl, with the exception of compounds in which $R^3$ is 3-chlorophenyl, 4-chlorophenyl, 2,4-dichlorophenyl or methylphenyl.

2. A process for combating fungi, wherein the fungi, or the materials, plants, seed or soil threatened by fungus attack are treated with a fungicidally effective amount of an acrylic ester of the formula:

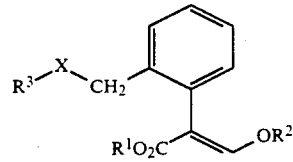

where $R^1$ and $R^2$ are hydrogen or $C_1$-$C_5$-alkyl, X is S, $R^3$ is unsubstituted naphthyl, unsubstituted phenanthrenyl, substituted phenyl, substituted naphthyl or substituted phenanthrenyl, wherein the substituents are halogen, cyano, nitro, formyl, $C_1$-$C_{10}$alkyl, $C_1$-$C_4$-alkoxy, $C_1$-$C_2$-haloalkyl, aryl or $C_1$-$C_4$-alkoxycarbonyl, with the exception of compounds in which $R^3$ is 3-chlorophenyl, 4-chlorophenyl, 2,4-dichlorophenyl or methylphenyl.

3. A fungicide containing an inert carrier and a fungicidally effective amount of an acrylic ester of the formula:

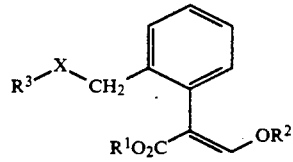

where $R^1$ and $R^2$ are hydrogen or $C_1$-$C_5$-alkyl, X is S, $R^3$ is unsubstituted naphthyl, unsubstituted phenanthrenyl, substituted phenyl, substituted naphthyl or substituted phenanthrenyl, wherein the substituents are halogen, cyano, nitro, formyl, $C_1$-$C_{10}$alkyl, $C_1$-$C_2$-haloalkyl, aryl or $C_1$-$C_4$-alkoxycarbonyl, with the exception of compounds in which $R^3$ is 3-chlorophenyl, 4-chlorophenyl, 2,4-dichlorophenyl or methylphenyl.

4. An acrylic ester as set forth in claim 1, where $R^1$ and $R^2$ are methyl, and $R^3$ is 2-naphthyl.

5. An acrylic ester as set forth in claim 1, where $R^1$ and $R^2$ are methyl, and $R^3$ is 2-chlorophenyl.

6. An acrylic ester as set forth in claim 1, where $R^1$ and $R^2$ are methyl, and $R^3$ is 2,5-dichlorophenyl.

7. An acrylic ester as set forth in claim 1, where $R^1$ and $R^2$ are methyl, and $R^3$ is 2-bromophenyl.

8. An acrylic ester as set forth in claim 1, where $R^1$ and $R^2$ are methyl, and $R^3$ is 3-bromophenyl.

* * * * *